(12) United States Patent
Schlenoff et al.

(10) Patent No.: US 7,101,947 B2
(45) Date of Patent: Sep. 5, 2006

(54) POLYELECTROLYTE COMPLEX FILMS FOR ANALYTICAL AND MEMBRANE SEPARATION OF CHIRAL COMPOUNDS

(75) Inventors: Joseph B. Schlenoff, Tallahassee, FL (US); Hassan Rmaile, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 383 days.

(21) Appl. No.: 10/462,164

(22) Filed: Jun. 16, 2003

(65) Prior Publication Data

US 2004/0044100 A1    Mar. 4, 2004

Related U.S. Application Data

(60) Provisional application No. 60/388,612, filed on Jun. 14, 2002.

(51) Int. Cl.
*C08F 20/06* (2006.01)

(52) U.S. Cl. .............. 526/348.1; 526/317.1; 526/303.1; 428/500; 428/515; 428/475.8; 210/198.2; 210/660; 210/654

(58) Field of Classification Search ............ 526/317.1, 526/303.1, 348.1; 428/483, 500, 515, 516, 428/624, 424.2, 475.8, 447; 210/198.2, 660, 210/654
See application file for complete search history.

(56) References Cited

U.S. PATENT DOCUMENTS

| | | | |
|---|---|---|---|
| 4,169,023 A | | 9/1979 | Sata et al. |
| 4,501,835 A | * | 2/1985 | Berke .................... 524/29 |
| 4,654,235 A | | 3/1987 | Effenberger et al. |
| 5,077,217 A | | 12/1991 | Matson et al. |
| 5,080,795 A | | 1/1992 | Pirkle et al. |
| 5,085,775 A | * | 2/1992 | Swamikannu .......... 210/500.27 |
| 5,208,111 A | | 5/1993 | Decher et al. |
| 5,336,298 A | | 8/1994 | Quinn et al. |
| 5,518,767 A | | 5/1996 | Rubner et al. |
| 5,536,573 A | | 7/1996 | Rubner et al. |
| 5,630,941 A | | 5/1997 | Burger et al. |
| 5,700,559 A | | 12/1997 | Sheu et al. |
| 5,711,915 A | * | 1/1998 | Siegmund et al. ......... 422/68.1 |
| 5,716,709 A | | 2/1998 | Ferguson et al. |
| 5,770,084 A | | 6/1998 | Warner et al. |
| 5,807,636 A | * | 9/1998 | Sheu et al. ................ 428/403 |
| 5,837,377 A | | 11/1998 | Sheu et al. |
| 5,964,794 A | | 10/1999 | Bolz et al. |
| 6,013,738 A | | 1/2000 | Daly et al. |
| 6,018,018 A | | 1/2000 | Samuelson et al. |
| 6,022,590 A | | 2/2000 | Ferguson et al. |
| 6,051,437 A | | 4/2000 | Luo et al. |
| 6,106,948 A | | 8/2000 | Wang et al. |
| 6,114,099 A | | 9/2000 | Liu et al. |
| 6,270,640 B1 | | 8/2001 | Warner et al. |
| 6,379,552 B1 | | 4/2002 | Kitagawa et al. |
| 6,402,918 B1 | | 6/2002 | Schlenoff et al. |
| H2046 H | | 9/2002 | Roberts et al. |
| 6,447,887 B1 | | 9/2002 | Claus et al. |
| 6,451,871 B1 | | 9/2002 | Winterton et al. |
| 6,468,657 B1 | | 10/2002 | Hou et al. |
| 6,479,146 B1 | | 11/2002 | Caruso et al. |
| 6,492,096 B1 | | 12/2002 | Liu et al. |
| 6,610,789 B1 | | 8/2003 | Watakabe et al. |
| 2002/0053514 A1 | * | 5/2002 | Locascio et al. ............ 204/454 |
| 2002/0130045 A1 | | 9/2002 | Schlenoff et al. |
| 2002/0187197 A1 | | 12/2002 | Caruso et al. |

FOREIGN PATENT DOCUMENTS

| | | |
|---|---|---|
| DE | 199 09 841 A1 | 9/2000 |
| EP | 1 116 516 A1 | 7/2001 |
| EP | 1 262 307 A2 | 12/2002 |
| WO | WO 99/35520 | 7/1999 |
| WO | WO 00/53296 | 2/2000 |
| WO | WO 01/57118 A2 | 8/2001 |
| WO | WO 01/92924 A1 | 12/2001 |
| WO | WO 02/17888 A2 | 3/2002 |
| WO | WO 02/096477 A2 | 12/2002 |
| WO | WO 02/097481 A1 | 12/2002 |

OTHER PUBLICATIONS

Cheng et al., J. Phys. Chem. B, 103, 8726-8731(1999).*
Baczuk et al., J. Chromatography A, 60, 351-361(1971).*
U.S. Appl. No. 10/283,471, filed Oct. 30, 2002, Warner et al.
Yufei Cheng and Robert M. Corn, Ultrathin Polypeptide Multilayer Films for the Fabrication of Model Liquid/Liquid Electrochemical Interfaces, J. Phys. Chem. B 1999, vol. 103, pp. 8726-8731, published Sep. 18, 1999.
Hanfa Zou, Xiaodong Huang, Mingliang Ye, Quanzhou Luo, Monolithic Stationary Phases for Liquid Chromatography and Capillary Electrochromatography, Journal of Chromatography A, vol. 954, pp. 5-32, published Apr. 5, 2002.
Constantina P. Kapnissi, Cevdet Akbay, Joseph B. Schlenoff, Isiah M. Warner, Analytical Separations Using Molecular Micelles in Open-Tubular Capillary Electrochromatography, Analytical Chemistry, vol. 74, No. 10, pp. 2328-2335, Published Apr. 20, 2002.

(Continued)

*Primary Examiner*—Ling-Sui Choi
(74) *Attorney, Agent, or Firm*—Senniger Powers

(57) ABSTRACT

The present invention is directed to enantioselective polyelectrolyte complex films. Further, said films may be free or isolated membranes, or coatings on substrates such a porous substrates, capillary tubes, chromatographic packing material, and monolithic stationary phases and used to separate chiral compounds. The present invention is also directed to a method for forming such enantioselective polyelectrolyte complex films.

15 Claims, 8 Drawing Sheets

OTHER PUBLICATIONS

Ph. Lavalle, C. Gergely, F. J. G. Cuisinier, G. Decher, P. Schaaf, J. C. Voegel, and C. Picart, Comparison of the Structure of Polyelectrolyte Multilayer Films Exhibiting a Linear and an Exponential Growth Regime: An in Situ Atomic Force Microscopy Study, American Chemical Society, Macromolecules 2002, vol. 35, pp. 4458-4465, Published Apr. 27, 2002.

Hassan H. Rmaile and Joseph B. Schlenoff, Optically Active Polyelectrolyte Multilayers as Membranes for Chiral Separations, J. Am. Chem. Soc., 2003, vol. 125, pp. 65602-6603; S1-S7, Published May 1, 2003.

* cited by examiner

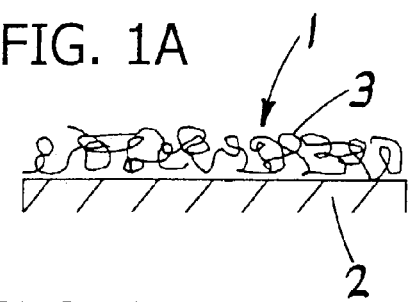
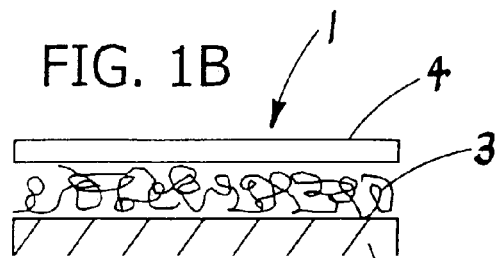
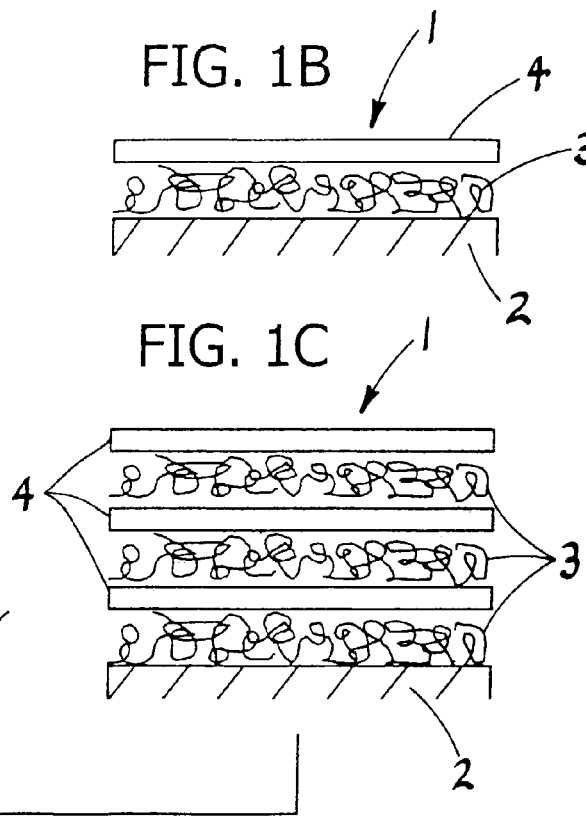
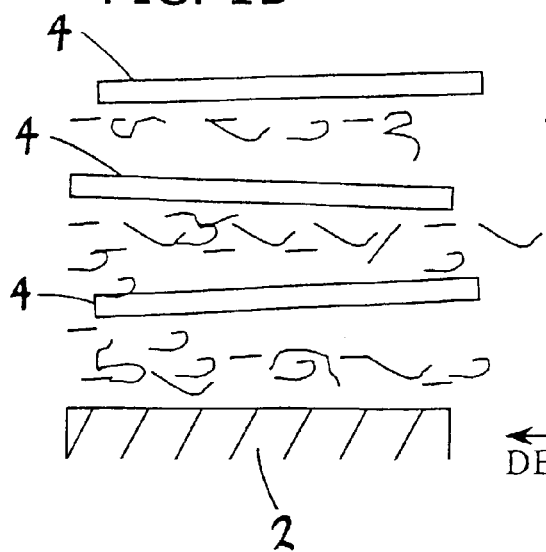

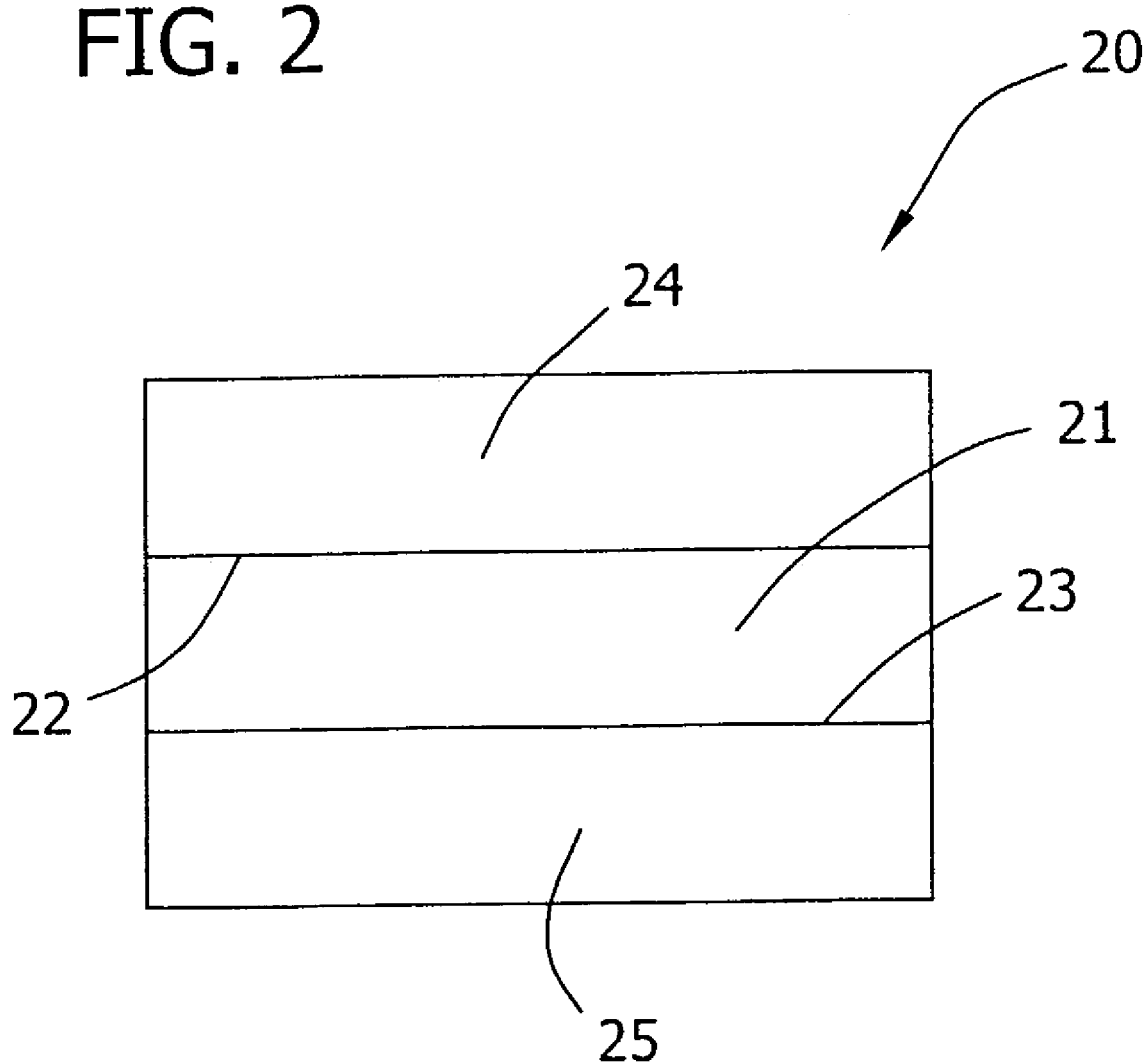

FIG. 3
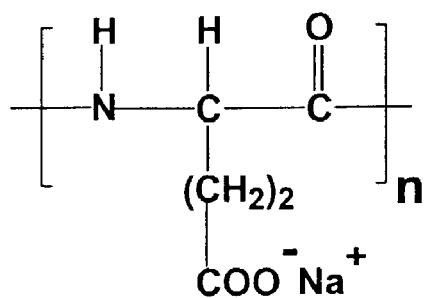
Poly(glutamic acid sodium salt), PGA
$pK_a \sim 4\text{-}5$
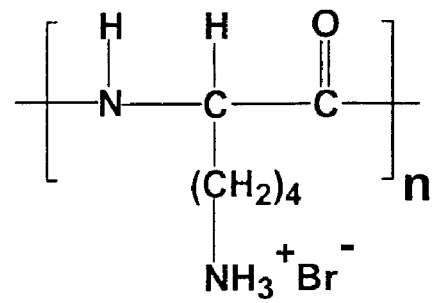
Poly(lysine hydrobromide), PL
$pK_a \sim 9\text{-}10$
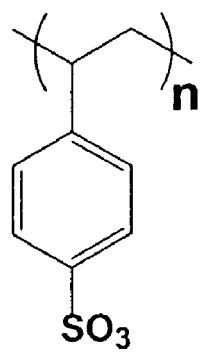
Poly(styrene sulfonate)
PSS
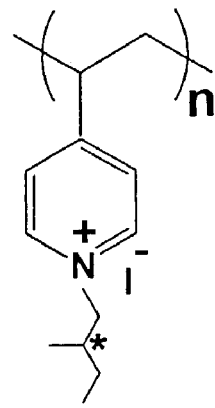
Poly(N-alkylated vinyl pyridine)
PN(S)4VP

FIG. 4
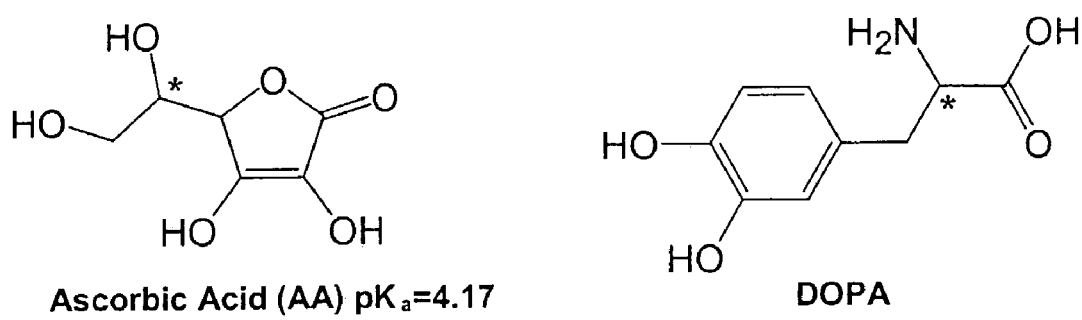
Ascorbic Acid (AA) $pK_a=4.17$    DOPA
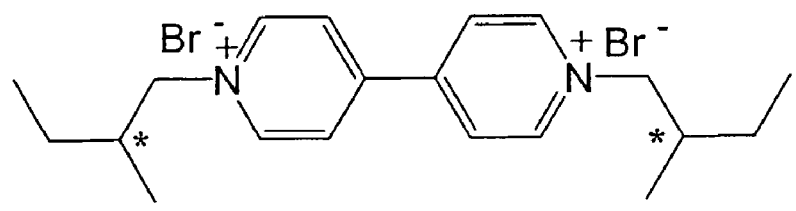
Optically active viologen
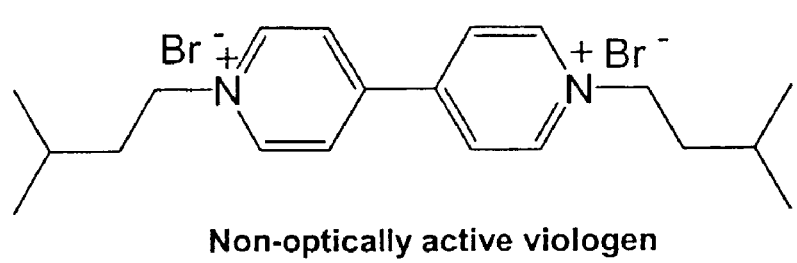
Non-optically active viologen

POLYELECTROLYTE COMPLEX FILMS FOR ANALYTICAL AND MEMBRANE SEPARATION OF CHIRAL COMPOUNDS

CROSS-REFERENCE TO RELATED APPLICATIONS

This application claims the benefit of U.S. Provisional Application No. 60/388,612, filed Jun. 14, 2002, which is incorporated herein by reference in its entirety.

BACKGROUND OF THE INVENTION

The present invention relates generally to the use of a thin film membrane or coating comprising charged polymers for the separation of optically active or chiral molecules.

The pharmaceutical industry must often produce drugs which are comprised of molecules which are chirally pure (i.e., the molecules are substantially all the same enantiomer). See Stenson, C&EN 45 (May 14, 2001). As such, methods for the commercial-scale separation of chiral forms are highly desirable. Chromatographic methods such as high performance liquid chromatography (HPLC), and supercritical fluid chromatography (SFC) have been used for chiral separation. However, chromatographic methods tend to be slow and labor intensive, and usually require specialized equipment such as simulated moving beds. Chiral separation may also be accomplished using membranes. In contrast to conventional chromatographic methods, chiral separation using one or more membranes offers the advantages of simplicity and higher throughput. Although chiral separation using conventional enantioselective membranes may be considered to be an improvement over conventional chromatographic separation methods, conventional enantioselective membranes are relatively thick (e.g., greater than 1 μm) which tends to reduce the permeation of molecules through the membranes. Additionally, conventional enantioselective membranes are formed by methods such as spray coating, dip coating, plasma polymerization, and chemical grafting which tend to be time consuming, costly, produce membranes which have a relatively high thickness variation, and exhibit low permeability.

Recently, ultrathin polymeric membranes have been prepared using charged polymers, or polyelectrolytes, which are alternately deposited on a substrate or substratum. See Decher and Schlenoff, Eds., *Multilayer Thin Films—Sequential Assembly of Nanocomposite Materials*, Wiley-VCH, Weinheim (2003); Decher, Science 277, 1232 (1997); and Decher, Hong, and Schmitt, Thin Solid Films 210/211, 831 (1992). For example, a buildup of multilayers may be accomplished by dipping, i.e., cycling a substrate between two reservoirs containing aqueous solutions of polyelectrolytes of opposite charge, with an optional rinse step in pure water following each immersion. Each cycle adds a layer of polymer via electrostatic forces to the oppositely-charged surface and reverses the surface charge thereby priming the film for the addition of the next layer. Films prepared in this manner tend to be uniform, follow the contours and irregularities of the substrate, and are typically between about 10 nm and about 10,000 nm thick. The thickness of a film depends on many factors, including the number of layers deposited, the ionic strength of the solutions, the types of polymers, the deposition time, and the solvent used. Although studies have shown that the substantial interpenetration of the individual polymer layers results in little composition variation over the thickness of a film, such polymer thin films are, nevertheless, referred to as polyelectrolyte multilayers (PEMUs).

Though recently developed, PEMUs are being used in a wide variety of fields including light emitting devices, nonlinear optics, sensors, enzyme active thin films, electrochromics, conductive coatings, patterning, anticorrosion coatings, antistatic coatings, lubricating films, biocompatibilization, dialysis, and as selective membranes for the separation of gaseous and dissolved ionic species. See Fou et al., J. Appl. Phys. 79, 7501 (1996); Decher et al., J. Biosens. Bioelect. 9, 677 (1994); Sun et al., Macromol. Chem. Phys. 197, 147 (1996); Onda et al., Biotech Bioeng 51, 163 (1996); Lvov et al., J. Am. Chem. Soc. 120, 40733 (1998); Laurent et al., Langmuir 13, 1552 (1997); Stepp et al., J. Electrochem. Soc. 144, L 55 (1997); Cheung et al., Thin Solid Films 244, 985 (1994); Hammond et al., Macromolecules 28, 7569 (1995); Huck et al., Langmuir 15, 6862 (1999); Stroeve et al., Thin Solid Films 284, 708 (1996); Levasalmi et al., Macromolecules 30, 1752 (1997); Harris et al., Langmuir 16, 2006 (2000); Krasemann et al., 16, 287 (2000); Harris et al., J. Am. Chem. Soc. 121, 1978 (1999); Harris et al., Chem. Mater. 12, 1941 (2000). In fact, PEMUs are particularly suited for use as selective membranes because they are uniform, rugged, easily prepared on a variety of substrates, continuous, resistant to protein adsorption, have reproducible thicknesses, may be made very thin to allow high permeation rates, and may be made from a wide range of compositions. See Graul et al., Anal. Chem. 71, 4007 (1999). In view of the foregoing PEMU attributes, a need exists to develop a method for separating chiral molecules that utilizes enantioselective polyelectrolyte complex membranes.

SUMMARY OF THE INVENTION

Briefly, therefore, the present invention is directed to an optically active polyelectrolyte complex comprising a positively-charged polyelectrolyte and a negatively-charged polyelectrolyte, wherein each polyelectrolyte is formed from a synthetic monomer and at least one of the polyelectrolytes comprises an enantiomeric excess of chiral repeat units.

The present invention is also directed to a polyelectrolyte complex comprising a positively-charged polyelectrolyte and a negatively-charged polyelectrolyte, wherein each polyelectrolyte is formed from a synthetic monomer and at least one of the polyelectrolytes comprises an enantiomeric excess of chiral repeat units.

Additionally, the invention is directed to a polyelectrolyte complex comprising a positively-charged polyelectrolyte and a negatively-charged polyelectrolyte, wherein at least one of the polyelectrolytes comprises a chiral cyclodextrin moiety.

Further, the invention is directed to a polyelectrolyte film. The film comprises a first stratum having a front surface and a back surface, the first stratum comprising a first positively-charged polyelectrolyte and a first negatively-charged polyelectrolyte, wherein at least one of the first polyelectrolytes is formed from a natural monomer. The films also comprises a second stratum on the front surface of the first stratum, the second stratum comprising a second positively-charged polyelectrolyte and a second negatively-charged polyelectrolyte, wherein the second positively- and negatively-charged polyelectrolytes are formed from synthetic monomers. Also, at least one of the first positively-charged polyelectrolyte, the first negatively-charged polyelectrolyte, the second positively-charged polyelectrolyte, and the second negatively-charged polyelectrolyte comprises an enantiomeric excess of chiral repeat units.

The present invention is also directed to a free membrane. The free membrane comprising a positively-charged polyelectrolyte and a negatively-charged polyelectrolyte, wherein at least one of the polyelectrolytes comprises an enantiomeric excess of chiral repeat units.

Additionally, the present invention is directed to a supported membrane. The supported membrane comprising a porous substratum having a surface and a polyelectrolyte complex on the surface of the porous substratum, the polyelectrolyte complex comprising a positively-charged polyelectrolyte and a negatively-charged polyelectrolyte, and at least one of the polyelectrolytes comprises an enantiomeric excess of chiral repeat units.

Further, the present invention is directed to a supported film. The supported film comprising a porous substratum having a surface and a polyelectrolyte complex on the surface of the porous substratum, the polyelectrolyte complex comprising a positively-charged polyelectrolyte and a negatively-charged polyelectrolyte, and at least one of the polyelectrolytes comprises a chiral cyclodextrin moiety.

The present invention is also directed to a chromatographic stationary phase. The chromatographic stationary phase comprising a substratum having a surface and a polyelectrolyte complex on the surface of the substratum, the polyelectrolyte complex comprising a positively-charged polyelectrolyte and a negatively-charged polyelectrolyte, and at least one of the polyelectrolytes comprises an enantiomeric excess of chiral repeat units.

Additionally, the present invention is directed to a method for preparing an optically active polyelectrolyte complex. The method comprising providing a substratum comprising a surface; applying a first solution comprising a first polyelectrolyte onto at least a portion of the substratum surface whereby the polyelectrolyte in the first solution is deposited onto the portion of the substratum surface to form a first polymer layer comprising the first polyelectrolyte; and applying a second solution comprising a second polyelectrolyte that is oppositely-charged from the first polyelectrolyte whereby the second polyelectrolyte is deposited onto the first polymer layer to form a second polymer layer comprising the second polyelectrolyte. The first and second solutions are applied until the desired number of first and second polymer layers are formed. Also, each polyelectrolyte is formed from a synthetic monomer and at least one of the polyelectrolytes comprises an enantiomeric excess of chiral repeat units.

Further, the present invention is directed to a method for preparing a polyelectrolyte complex. The method comprising providing a substratum comprising a surface; applying a first solution comprising a first polyelectrolyte onto at least a portion of the substratum surface whereby the polyelectrolyte in the first solution is deposited onto the portion of the substratum surface to form a first polymer layer comprising the first polyelectrolyte; applying a second solution comprising a second polyelectrolyte that is oppositely-charged from the first polyelectrolyte whereby the second polyelectrolyte is deposited onto the first polymer layer to form a second polymer layer comprising the second polyelectrolyte; applying the first and second solutions until the desired number of first and second polymer layers are formed. Also, each polyelectrolyte is formed from a synthetic monomer, and at least one of the polyelectrolytes comprises an enantiomeric excess of chiral repeat units.

Further, the present invention is directed to a method for depositing a polyelectrolyte complex on a surface of a substratum. The method comprises applying a solution that comprises the polyelectrolyte complex onto at least a portion of the surface of the substratum whereby the polyelectrolyte complex is deposited onto the portion of the surface of the substratum, wherein the polyelectrolyte complex comprises a positively-charged polyelectrolyte and a negatively-charged polyelectrolyte, each polyelectrolyte is formed from a synthetic monomer, and at least one of the polyelectrolytes comprises an enantiomeric excess of chiral repeat units.

Still further, the present invention is directed to a method for depositing a polyelectrolyte complex on a surface of a substratum. The method comprises applying a solution that comprises the polyelectrolyte complex onto at least a portion of the surface of the substratum whereby the polyelectrolyte complex is deposited onto the portion of the surface of the substratum, wherein the polyelectrolyte complex comprises a positively-charged polyelectrolyte and a negatively-charged polyelectrolyte, and at least one of the polyelectrolytes comprises a chiral cyclodextrin moiety.

Additionally, the present invention is directed to a method of chromatographically separating test enantiomers. The method comprises using an optically active polyelectrolyte complex as a chiral surface which interacts with the test enantiomers in an enantioselective manner, the optically active polyelectrolyte complex comprising a positively-charged polyelectrolyte and a negatively-charged polyelectrolyte, wherein at least one of the polyelectrolytes comprises an enantiomeric excess of chiral repeat units.

Further, the present invention is directed to a method of separating test enantiomers. The method comprises using polyelectrolyte complex as a chiral surface which interacts with the test enantiomers in an enantioselective manner, the polyelectrolyte complex comprising a positively-charged polyelectrolyte and a negatively-charged polyelectrolyte, wherein at least one of the polyelectrolytes comprises an enantiomeric excess of chiral repeat units.

Still further, the present invention is directed to a method of separating test enantiomers. The method comprises using polyelectrolyte complex as a chiral surface which interacts with the test enantiomers in an enantioselective manner, the polyelectrolyte complex comprising a positively-charged polyelectrolyte and a negatively-charged polyelectrolyte, wherein at least one of the polyelectrolytes comprises a chiral cyclodextrin moiety.

The foregoing and other features and aspects of the present invention will become more apparent from the following description and accompanying figures.

BRIEF DESCRIPTION OF THE DRAWINGS

FIG. 1 depicts a releaseable membrane structure.

FIG. 2 depicts a protective membrane structure.

FIG. 3 contains the chemical drawings of several polyelectrolytes described herein.

FIG. 4 contains the chemical drawings of several probe molecules described herein (optical centers are indicated with a star).

DETAILED DESCRIPTION OF THE INVENTION

Figure 5:
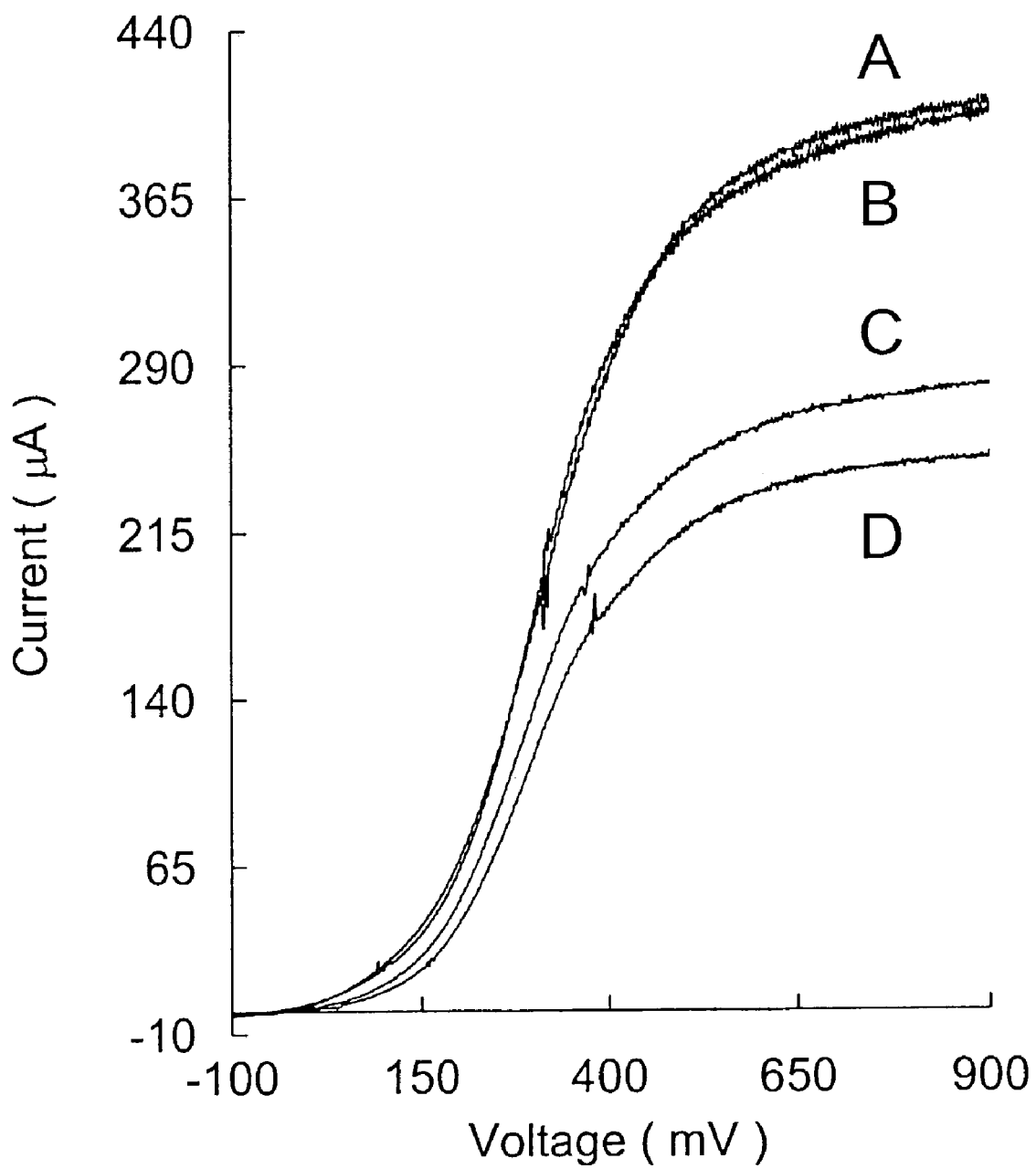
FIG. 5 is a graph containing linear scan voltammograms: the A line is that of an uncoated platinum disc electrode for D-ascorbic acid; the B line is that of an uncoated platinum disc electrode for L-ascorbic acid; the C line is that of a platinum disc electrode coated a PDGA/PDL multilayer having a thickness of about 90 nm for D-ascorbic acid; and the D line is that of a platinum disc electrode coated with a PDGA/PDL multilayer having a thickness of about 90 nm for L-ascorbic acid.

In general, the present invention is directed to the preparation of a coating or membrane comprising positively and a negatively charged polymers, one or both of which comprises a chemical sub-unit, which permits the separation of chemicals having different optical activities (i.e., the different enantiomers of a chiral chemical compound may be separated). In another embodiment the present invention is directed to the preparation of a coating or membrane comprising positively and a negatively charged polymers, one or both of which comprises an optically active chemical sub-unit, which permits the separation of chemicals having different optical activities.

The oppositely charged polymers (i.e., polyelectrolytes) used to form the films are water and/or organic soluble and comprise a monomer unit that is positively or negatively charged. The polyelectrolytes used in the present invention may be copolymers that have a combination of charged and/or neutral monomers (e.g., positive and neutral; negative and neutral; positive and negative; or positive, negative and neutral). Regardless of the exact combination of charged and neutral monomers, a polyelectrolyte of the present invention is predominantly positively charged or predominantly negatively charged and hereinafter is referred to as a "positively-charged polyelectrolyte" or a "negatively-charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDAD-co-PAC (i.e., poly(diallyldimethylammonium chloride) and polyacrylamide copolymer) in which the PDAD units have a charge of 1 and the PAC units are neutral so the average charge per repeat unit is less than 1.

The charges on a polyelectrolyte may be derived directly from the monomer units or they may be introduced by chemical reactions on a precursor polymer. For example, PDAD is made by polymerizing diallyldimethylammonium chloride, a positively charged water soluble vinyl monomer. PDAD-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about −0.8.

Examples of a negatively-charged polyelectrolyte include polyelectrolytes comprising a sulfonate group ($-SO_3^-$), such as poly(styrenesulfonic acid) (PSS), poly(2-acrylamido-2-methyl-1-propane sulfonic acid) (PAMPS), sulfonated poly (ether ether ketone) (SPEEK), sulfonated lignin, poly(ethylenesulfonic acid), poly(methacryloxyethylsulfonic acid), their salts, and copolymers thereof; polycarboxylates such as poly(acrylic acid) (PAA) and poly(methacrylic acid); and sulfates such as carrageenin.

Examples of a positively-charged polyelectrolyte include polyelectrolytes comprising a quaternary ammonium group, such as poly(diallyldimethylammonium chloride) (PDAD), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), other poly(N-alkylvinylpyridines), and copolymers thereof; and protonated polyamines such as poly(allylaminehydrochloride) (PAH) and polyethyleneimine (PEI).

Further examples of oppositely-charged polyelectrolytes include charged biomacromolecules which are naturally occurring polyelectrolytes or their charged derivatives. A positively-charged biomacromolecule comprises a protonated sub-unit (e.g., protonated amines). Some negatively charged biomacromolecules comprise a deprotonated sub-unit (e.g., deprotonated carboxylates). Examples of biomacromolecules which may be charged for use in accordance with the present invention include proteins, polypeptides, enzymes, DNA, RNA, heparin, alginic acid, chondroitin sulfate, chitosan, chitosan sulfate, cellulose sulfate, polysaccharides, dextran sulfate and carboxymethylcellulose.

The molecular weight of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomolecules), however, can reach as high as 10,000,000 grams/mole. The polyelectrolyte typically comprises about 0.01% to about 40% by weight of a polyelectrolyte solution, and preferably about 0.1% to about 10% by weight.

Many of the foregoing polymers/polyelectrolytes, such as PDAD, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention.

Many of the foregoing polyelectrolytes have a very low toxicity. In fact, poly(diallyldimethylammonium chloride), poly(2-acrylamido-2-methyl-1-propane sulfonic acid) and their copolymers are used in the personal care industry, e.g., in shampoos. Also, because the polyelectrolytes used in the method of the present invention are synthetic or synthetically modified natural polymers, their properties (e.g., charge density, viscosity, water solubility and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays a less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNM4VP) is considered to be hydrophilic, whereas polyvinyl pyridine alkylated with an octyl group (PNO4VP) is considered to be hydrophobic. Thus, water is preferably used as the solvent for hydrophilic polyelectrolytes and organic solvents such as ethanol, methanol, dimethylformamide, acetonitrile, carbon tetrachloride, and methylene chloride are preferably used for hydrophobic polyelectrolytes. Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids) their salts, and copolymers thereof; as well as poly(diallyldimethylammonium chloride), poly(vinylbenzyltrimethylammonium), ionenes, poly(acryloxyethyltrimethyl ammonium chloride), poly(methacryloxy(2-hydroxy) propyltrimethyl ammonium chloride), and copolymers thereof; and polyelectrolytes comprising a pyridinium group, such as, poly(N-methylvinylpyridium), protonated polyamines, such as, poly(allylamine hydrochloride) and poly(ethyleneimmine). Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly (styrenesulfonic acid), poly(diallyldimethylammonium chloride), poly(N-methylvinylpyridinium) and poly(ethyleneimmine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate.

In one embodiment the negatively-charged polyelectrolyte is selected from the group consisting of poly(styrenesulfonic acid), poly(2-acrylamido-2-methyl-1-propane sulfonic acid), sulfonated lignin, poly(ethylenesulfonic acid), poly(methacryloxyethylsulfonic acid), sulfonated poly(ether ether ketone), and poly(acrylic acid). In another embodiment the positively-charged polyelectrolyte is selected from the group consisting of poly(diallyldimethylammonium chloride), poly(vinylbenzyltrimethylammonium chloride), ionenes, poly(acryloxyethyltrimethyl ammonium chloride), poly(methacryloxy(2-hydroxy)propyltrimethyl ammonium chloride), poly(N-methylvinylpyridinium), other poly (N-alkylvinyl pyridiniums), a poly(N-aryl vinyl pyridinium) and poly(allylaminehydrochloride)

Some polyelectrolytes used in accordance with the present invention generally become charged at certain pH values. For example, poly(acrylic acids) and derivatives begin to take on a negative charge within the range of about 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below about 8. As such, and in accordance with the present invention, the pH of a polyelectrolyte solution may be adjusted by the addition of an acid and/or base in order to attain, maintain, and/or adjust the electrical charge of a polyelectrolyte.

The term chiral refers to a molecule that is not superimposable on its mirror image (i.e., the molecule does not posses a plane of symmetry). Most chiral organic molecules contain one or more stereogenic centers which are carbon atoms that are bonded to 4 different groups. The pair of non-superimposable mirror images are generally referred to as enantiomers. A solution, mixture, or substance that comprises an excess of an enantiomer is often referred to as being optically active. That is, the plane of polarization of a beam of plane polarized light passed through the solution or mixture containing an excess of one chiral form of a molecule is typically rotated. Specifically, an enantiomer that rotates the plane of polarized light clockwise (to the right) as seen by an observer is dextrorotatory (indicated as D or +) and an enantiomer that rotates the plane of polarized light counterclockwise (to the left) is levorotatory (indicated as L or −). Because of this optical activity, enantiomers are often referred to as optical isomers or optically active.

Chirality may be obtained by polymerizing monomer units that are already chiral, or by reacting a non-chiral polymer with a chiral reagent, or with a reagent that, together with the existing polymer, introduces chirality on the polymer. An example of a chiral monomer is a chiral amino acid such as L- or D-glutamic acid or L- or D-lysine. Positively-charged synthetic chiral monomers may be made, for example, by reacting a vinyl pyridine or a vinyl amine with a chiral alkylating agent. Examples of vinyl amines include allylamine and diallylamine. After chiral modification the vinyl or allyl ammonium or vinyl pyridinium monomer may be polymerized to yield a chiral polyelectrolyte. Alternatively, the vinyl amine, allyl amine, or vinyl pyridine may be first polymerized then the polymer may be reacted with a chiral or non-chiral agent to yield a chiral polyelectrolyte. For example, a non-chiral poly(vinylpyridine) may be reacted with a chiral alkylating reagent such as a chiral alkyl halides (e.g., bromo, chloro, and iodo alkanes) and/or a chiral aryl halogen which results in the addition of a chiral center on the repeat units. Alkylation of a pyridine or an amine refers to reaction of a pyridine or amine with a linear or branched hydrocarbon comprising 1–18 carbons, generally, and a leaving group such as chlorine, bromine, iodine, or tosylate which is subject to displacement by a nucleophile such as the lone electron pairs on pyridine or an amine. Arylation of a pyridine or amine refers to reaction of a pyridine or amine with an active aryl group such as benzyl chloride or benzyl bromide. Similarly, negative polyelectrolytes may be prepared by sulfonating chiral monomers and then polymerizing these monomers, or by first polymerizing the monomers then sulfonating them. Alternatively, chiral monomers comprising carboxylate groups may be synthesized then polymerized to give polycarboxylate polyelectrolytes that are chiral. Further, a chiral polyelectrolyte may be formed by creating a charge on a chiral polymer. For example, certain chiral polyesters may be hydrolyzed to yield charged chiral polycarboxylates.

In one embodiment of the present invention a polyelectrolyte comprising an enantiomeric excess of chiral repeat units may be formed by polymerizing chiral monomer units. Although some monomer units may be naturally chiral (e.g., some amino acids and some cylodextrins), chirality may be imparted or introduced non-chiral, or achiral, monomer units such as a vinyl pyridine, a vinyl benzyl halide, a vinyl amine, and an allyl amine.

Cyclodextrins (CDs) are well known additives for the chromatographic separations of chiral compounds. Cyclodextrins are cyclic oligosaccharides, composed of glycopyranose monomer units, featuring a well-defined cavity. Enantiomeric resolution of solutes that fit within the cavity, which is chiral due to the optical activity of the composite carbohydrate moieties, is therefore achieved due to the more favorable interactions of the proper solute enantiomer with the cyclodextrin. See Beale, Analytical Chemistry, 70, 279R (1998). Cyclodextrins may be neutral, positively charged, or negatively charged.

Appropriate polymerization methods include radical polymerization, ring opening metathesis polymerization (ROMP), acyclic diene metathesis polymerization (ADMET) and condensation polymerization.

The degree of chirality is typically quantified in terms of percent enantiomeric excess (% ee) which is determined by dividing the measured specific rotation of an enantiomeric mixture by the specific rotation for the chirally pure enantiomer and multiplying by one hundred. Thus, the degree of chirality ranges from 0% ee for racemic mixtures to 100% ee for a chirally pure material. The chiral selectivity of a film, membrane, or coating tends to depend, at least in part, on the enantiomeric excess, and as such, films or membranes comprising polyelectrolytes having the highest % ee as possible are typically preferred. In one embodiment of the present invention the polyelectrolyte has degree of chirality that is between greater than 0 and 100% ee. In additional embodiments the polyelectrolyte has a degree of chirality that is between about 10 and about 90% ee, between about 20 and about 70% ee, or between about 30 and about 60% ee.

Optionally, the polyelectrolyte solutions may comprise one or more "salts." A "salt" is defined as a soluble, ionic, inorganic compound that dissociates to stable ions (e.g., sodium chloride). A salt is included in the polyelectrolyte solutions to control the thickness of the adsorbed layers. More specifically, including a salt increases the thickness of the adsorbed polyelectrolyte layer. In general increasing the salt concentration increases the thickness of the layer for a given spray coverage and contact time. This phenomenon is limited, however, by the fact that upon reaching a sufficient salt concentration multilayers tend to dissociate. Typically, the amount of salt added to the polyelectrolyte solution is about 10% by weight or less.

An optically active coating of the present invention may be formed by exposing a surface to alternating oppositely charged polyelectrolyte solutions. This method, however, does not generally result in a layered morphology of the polymers with the film. Rather, the polymeric components interdiffuse and mix on a molecular level upon incorporation into the thin film. See Lösche et al., Macromolecules 31, 8893 (1998). Thus, the polymeric components form a true molecular blend, referred to as a "polyelectrolyte complex," with intimate contact between polymers driven by the strong electrostatic complexation between positive and negative polymer segments. The complexed polyelectrolyte within the film has the same amorphous morphology as a polyelectrolyte complex formed by mixing solutions of positive and negative polyelectrolyte. It is also known that although there is extensive intermingling of neighboring layers over a range of 4–6 nominal layers, is it possible to obtain actual layers of different composition, or strata, by interspersing several layers made from one pair of polyelectrolytes by several layers made from a different pair. See Lösche et al., Macromolecules 31, 8893 (1998). For example, if polymers A and C are positively charged and polymers B and D are negatively charged, about 3 or 4 pairs of A/B layers followed by about 3 or 4 pairs of A/D or C/D layers will produce two strata of distinct composition.

Alternatively, the optically active coating may be applied to a surface using a pre-formed polyelectrolyte complex. See Michaels, *Polyelectrolyte Complexes*, Ind. Eng. Chem. 57, 32–40 (1965). This is accomplished by mixing the oppositely-charged polyelectrolytes to form a polyelectrolyte complex precipitate which is then dissolved or re-suspended in a suitable solvent/liquid to from a polyelectrolyte complex solution/dispersion. The polyelectrolyte complex solution/dispersion is then applied to the substrate surface and the solvent/liquid is evaporated, leaving behind a film comprising the polyelectrolyte complex.

The polyelectrolyte solutions and/or polyelectrolyte complex may be deposited on a substrate by any appropriate method such as casting, dip coating, doctor blading, and/or spraying. Particularly preferred methods are dip coating and spraying. Spraying is especially preferred when applying the coating using alternating exposure of oppositely-charged polyelectrolyte solutions. Spraying alternating oppositely-charged polyelectrolyte solutions has several advantages including: improved control over film thickness especially the ability to make extremely thin thicknesses (e.g., less than about 1 µm), enhanced uniformity of film thickness especially over uneven surfaces and contours, and films may be produced without the use of organic solvents which may require precautions to avoid negative health and/or environmental consequences. The solutions may be sprayed onto a substrate by any applicable means (e.g., an atomizer, an aspirator, ultrasonic vapor generator, entrainment in compressed gas). In fact, a hand operated "plant mister" has been used to spray the polyelectrolyte solutions. Typically, the droplet size in the spray is about 10 nm to about 1 mm in diameter. Preferably, the droplet size is about 10 µm to 100 µm in diameter. The coverage of the spray is typically about 0.001 to 1 $mL/cm^2$, and preferably about 0.01 to 0.1 $mL/cm^2$.

The duration in which the polyelectrolyte solution is typically in contact with the surface it is sprayed upon (i.e., the contact time) varies from a couple seconds to several minutes to achieve a maximum, or steady-state, thickness. The contact duration is selected based on the desired relationship between throughput (i.e., the rate at which alternating layers are created) and layer thickness. Specifically, decreasing the contact duration increases throughput and decreases layer thickness whereas increasing the duration decreases throughput and increases thickness. Preferably, the contact time is selected to maximize the throughput of layers that have a satisfactory thickness and are uniform across the surface.

The oppositely-charged polyelectrolyte solutions may be sprayed immediately after each other without an intermediate rinse step, however, experimental results to date indicate that the films, though thicker, are of poorer quality (e.g., blobs, poor adhesion, and non-uniform film thickness). Additionally, the composition of deposited layers depends precisely on the amount of spray that impinges on the substrate and can lead to non-stoichiometric (the ratio is not controlled) complexes. Including an intermediate rinse step between the spraying of the oppositely-charged polyelectrolyte solutions, however, rinses off excess, non-bonded, polyelectrolyte and decreases, or eliminates, the formation of blobs, poor adhesion and non-uniform film thickness. Rinsing between the application of each polyelectrolyte solution also results in stoichiometric complexes. The rinsing liquid comprises an appropriate solvent (e.g., water or organic solvent such as alcohol). Preferably the solvent is water. If the solvent is inorganic (e.g., water), the rinsing liquid may also comprise an organic modifier (e.g., ethanol, methanol or propanol). The concentration of organic modifier can be as high as less than 100 percent by weight of the rinsing liquid, but is preferably less than about 50 percent by weight. The rinsing liquid may also comprise a salt (e.g., sodium chloride) which is soluble in the solvent and the organic modifier, if included in the rinsing liquid. The concentration of salt is preferably below about 10 percent by weight of the rinsing liquid. It should be noted that as the concentration of organic modifier increases the maximum solubility concentration of salt decreases. The rinsing liquid, however, should not comprise a polyelectrolyte. The rinsing step may be accomplished by any appropriate means (e.g., dipping or spraying). Preferably, the rinsing step is accomplished by spraying. Although rinsing removes much of the polymer in the layer of liquid wetting the surface, the amount of waste is preferably reduced by recycling the polymer solutions removed from the surface. Optionally, prior to depositing the second through $n^{th}$ layer of sprayed oppositely charged polyelectrolyte solution, the surface of the multilayer structure may be dried.

Both dip coating and spraying permit a wide variety of additives to be incorporated into a film as it is formed. Additives that may be incorporated into polyelectrolyte multilayers include inorganic materials such as metallic oxide particles (e.g., silicon dioxide, aluminum oxide, titanium dioxide, iron oxide, zirconium oxide and vanadium oxide) and clay minerals (e.g., hectorite, kaolin, laponite and montmorillonite). For example, nanoparticles of zirconium oxide added to a polyelectrolyte solution or complex solution tend to improve the abrasion resistance of the deposited film. See Rosidian et al., *Ionic Self-assembly of Ultra Hard ZrO$_2$/polymernanocomposite Films*, Adv. Mater. 10, 1087–1091.

When immersed in the solvent of the polyelectrolyte solutions, such additives take on a charge which is typically negative. More precisely, when an insoluble solid is contacted with a liquid medium, an electric double layer forms at the solid-liquid interface. The electric double layer comprises an array of either positive or negative ions attached to, or adsorbed on, the surface of the solid and a diffuse layer of ions of opposite charge surrounding the charged surface of the solid and extending into the liquid medium. The electric potential across the electric double layer is known as the zeta potential. Both the magnitude and polarity of the zeta potential for a particular solid-liquid system will tend to vary depending on the composition of the solid surface and the liquid, as well as other factors, including the size of the solid and the temperature and pH of the liquid. Although the polarity of the zeta potential may vary from one particle to another within a suspension of solid particles in a liquid, the polarity of the zeta potential for the suspension as a whole is characterized by the polarity of the surface charge attached to a predominant number of solid particles within the suspension. That is, a majority of the insoluble particles in the suspension will have either a positive or negative surface charge. The magnitude and polarity of the zeta potential for a suspension of solid particles in a liquid is calculated from the electrophoretic mobilities (i.e., the rates at which solid particles travel between charged electrodes placed in the suspension) and can be readily determined using commercially available microelectrophoresis apparatus. If present, the concentration of inorganic materials preferably does not exceed about 10% by weight of a polyelectrolyte solution and more preferably the concentration is between about 0.01% and about 1% by weight of the polyelectrolyte solution.

In accordance with one embodiment of the present invention, chiral multilayers may be constructed from individual polyelectrolytes which are chiral. These chiral multilayers, when used as membranes for separations, exhibit preferential permeability between chiral forms of molecules to be separated.

In view of the foregoing, in one embodiment a polyelectrolyte complex comprising at least one polyelectrolyte that comprises an enantiomeric excess of chiral repeat units is formed. In another embodiment a PEMU comprising at least one chiral layer may be constructed from at least one polyelectrolyte which comprises an enantiomeric excess of chiral repeat units. In yet another embodiment of the present invention, each positively- or negatively-charged polyelectrolyte comprises an enantiomeric excess of chiral repeat units. In still another embodiment both the positively- and the negatively-charged polyelectrolytes comprise an enantiomeric excess of chiral repeat units, and the enantiomeric excess chiral repeat units are the same chirality (i.e., both are L or D). A polyelectolyte complex, in general, and a PEMU, in particular, comprising a chiral polyelectrolyte tends to exhibit preferential permeability between chiral forms of a molecule and may be used as a chiral separation coating and/or membrane. It is to be noted that the enantioselectivity of a particular polyelectrolyte complex may depend on factors such as the particular enantiomers to be separated (i.e., test enantiomers) and the physical form of the polyelectrolyte complex (e.g., membrane or coating).

In one embodiment of the present invention the polyelectrolyte complex is a coating or layer on a substrate or substratum and may be deposited according to any appropriate method (see, e.g., supra, as a multilayer or as a pre-formed polyelectrolyte complex). The substratum may be non-porous or porous and may be comprised of many types of materials that are well know in the art such as polymers, metals, and ceramics. The surface of polymeric support materials may be positively charged by comprising tetraalkyl ammonium groups, negatively charged by comprising sulfonate groups, or neutral. In another embodiment the substratum is porous and comprises a material selected from the group consisting of polypropylene, nylon, polytetrafluoroethylene, glass, and alumina (all of which are known to those of skill in the art). The porosity of the substratum is sufficient to allow transport of test enantiomers through the substratum. Typically, the average size of the pores is between about 100 nm and about 10 μm and the degree of porosity is between about 0.1 and about 60%. In yet another embodiment the polyelectrolyte complex is deposited on or adsorbed to at least a portion of the surface of the stationary phase of a chromatographic medium such as particulate chromatographic column packing material, the interior of capillary tubes as used for capillary electrophoresis chromatography (see, U.S. Pat. No. 6,402,918 and U.S. Pat. App.

Pub. No. US2002/0130045 A1 which are hereby incorporated by reference in their entireties for all purposes), or a porous continuous solid often referred to as a monolithic stationary phase (see Zou et al., *Monolithic stationary phased for liquid chromatography and capillary electro-chromatography*, Journal of Chromatography A, 954, 5–32 (2002)).

In another embodiment the polyelectrolyte complex is a free, or isolated, membrane. Typically, an isolated membrane comprising a polyelectrolyte complex is formed by depositing the complex on a support and then dissolving the support. For example, a cellulose acetate support may be dissolved with acetone to remove it from a multilayer comprising charged particles and polymers. See Mamedov et al., Langmuir 16, 5530 (2000). This process typically has characteristics that are often considered to be drawbacks. For example, it may be slow, typically requires disposal of organic solvents, it destroys the substratum, may be difficult or impossible to employ on a multilayer membrane which does not contain charged particles, and may denature, or deactivate, biologically-derived species (e.g., enzymes) incorporated Within the membrane.

Alternatively, isolated membranes may be produced by using a release stratum that has a composition that is different from the remainder of the membrane, the release stratum is designed to decompose, dissociate or become weakly associated under certain conditions (e.g., a change in salt concentration, pH and/or temperature) thereby freeing the membrane from a substratum. This approach was set forth in U.S. Prov. Appln 60/284,723 for achiral polyelectrolytes which is hereby incorporated by reference in its entirety for all purposes. Referring to FIG. 1A, a releaseable membrane structure 1 for producing a free membrane comprises a substratum or support 2 and a release stratum 3 deposited on the substratum as depicted. Referring to FIG. 1B, a membrane stratum 4 is deposited on the release stratum 3. The time and cost associated with preparing the free membranes of the present invention may be decreased by depositing multiple membrane stratum 4 on the substratum 2 each being separated by a release stratum 3 as depicted in FIG. 1C. In turn, each stratum comprises at least two oppositely-charged polyelectrolytes and is preferably a laminate of alternating oppositely-charged polyelectrolytes applied as layers. Due to the extensive interpenetration of neighboring oppositely-charge polyelectrolyte amongst the layers, each stratum is preferably at least several layers of thick (e.g., at least about 6 oppositely-charged polyelectrolyte layers and more preferably at least about 10 oppositely-charged polyelectrolyte layers). Selective decomposition of the oppositely-charged polyelectrolytes of the release stratum affords controlled separation of high quality free membranes 4 as depicted in FIG. 1D. Examples of release stratum polyelectrolytes and dissociation stimuli include PSS/PDAD and a NaCl solution $\geq$about 3.5 M; PAA/PDAD and NaCl solution $\geq$about 0.6 M; and PSS/PDAD-co-PAA and a solution having a pH $\geq$6. Thus, depending on the desired polyelectrolyte free membrane, the appropriate oppositely-charged polyelectrolytes may be selected to create a release stratum that decomposes, dissociates, or becomes weakly associated under conditions which do not negatively impact the integrity of the free membrane.

Polyelectrolytes formed from synthetic monomers such as poly(styrenesulfonic acid) and poly(acrylic acid) may, depending on the application, be preferred over polyelectrolytes formed from natural monomers. Specifically, films, coatings, or membranes comprising polyelectrolytes formed from natural monomers such as lysine and glutamic acid may be degraded upon being exposed to microorganisms. If, however, a film formed from one or more natural monomers is desired, the film or coating comprising at least one polyelectrolyte formed from a natural monomer may be protected by applying a protective layer, film, stratum, or covering comprising polyelectrolytes formed from synthetic monomers to prevent contact between microorganisms and the interior, covered, or protected polyelectrolyte(s) formed from a natural monomer(s). Referring to FIG. 2, the film 20 may comprise a first stratum 21 (usually having a thickness equal to several layers as set forth above in the release stratum embodiment) having a front surface 22 and a back surface 23 in contact with optional substratum 25. The first stratum 21 comprises a first positively-charged polyelectrolyte and a first negatively-charged polyelectrolyte, wherein at least one of the first polyelectrolytes is formed from a natural monomer. On the front surface 22 of the first stratum 21 is a second stratum 24 (usually having a thickness equal to several layers) that comprises a second positively-charged polyelectrolyte and a second negatively-charged polyelectrolyte in which both of the second polyelectrolytes are formed from synthetic monomers. Further, at least one of the first positively-charged polyelectrolyte, the first negatively-charged polyelectrolyte, the second positively-charged polyelectrolyte, or the second negatively-charged polyelectrolyte comprise an enantiomeric excess of chiral repeat units. In another embodiment both of the first polyelectrolytes comprise an enantiomeric excess of chiral repeat units. In yet another embodiment the first polyelectrolytes have the same chirality (i.e., they are both L- or D-polyelectrolytes). In still another embodiment both of the second polyelectrolytes comprise an enantiomeric excess of chiral repeat units. In still another embodiment the second polyelectrolytes have the same chirality. The strata may be formed, for example, according to the oppositely-charged multilayer buildup technique or by the application of a pre-formed polyelectrolyte complex.

The present invention is also directed to the use of the above-described polyelectrolyte-containing coatings, films, or membranes for separating or resolving test enantiomers by any appropriate method. Exemplary methods include membrane separation and column separation. Column separation methods are typically referred to as a chromatography. Several chromatography methods are well known in the art, and as such, the apparatuses and operational parameters for carrying out a chromatographic separation are not set forth herein. See, e.g., Schlenoff et al., U.S. Pat. No. 6,402,918. In general, the separation of test enantiomers is accomplished by contacting said test enantiomers with a film, layer, coating, membrane (supported or unsupported) comprising a polyelectrolyte complex which interacts with the test enantiomers in an enantioselective manner. For example, a membrane comprising a polyelectrolyte complex wherein one or both of the oppositely-charged polyelectrolytes comprises an enantiomeric excess of chiral repeat units (L or D) when contacted with a sample comprising L- and D-test enantiomers may be selective for either the L-test enantiomer or the D-test enantiomer. As set forth in greater detail in the Examples, the selectivity mechanism may be based on kinetics, thermodynamics, and/or permeability of the enantioselective polyelectrolyte complex.

The present invention is further illustrated by the following examples which are merely for the purposes of illustration and are not to be regarded as limiting the scope of the invention or manner in which it may be practiced.

EXAMPLES

A. Permeability and Selectivity Analysis of Chiral PEMUs

A study of chiral permeability and selectivity of PEMUs constructed of polyelectrolytes having L- and D-chiral forms. Specifically, PEMUs were constructed of the polypeptides poly(lysine) (PL) and poly(glutamic acid) (PGA), and of the polyelectrolytes poly(N-(S)-2-methylbutyl-4-vinyl pyridinium iodide) (PN(S)4VP) which is a chiral alkylated polypyridine and poly(styrene sulfonate) (PSS). Chemical drawings of the above polyelectrolytes are depicted in FIG. 3. The multilayers were constructed on rotating disk electrodes, which permitted precise flux measurements of electroactive probes according to an alternating exposure method that is well known in the art. See Farhat et al., J. Am. Chem. Soc. 125, 4627 (2003). The chiral probes used in this study were L- or D-ascorbic acid (the former is Vitamin C), 3-3(3,4-dihydroxyphenyl)-L/D-alanine (DOPA), and a chiral viologen (a geometric isomer, rather than an enantiomer). Chemical drawings of the probes are depicted in FIG. 4. An additional experimental variable was the concentration of salt in the supporting electrolyte, which has been shown to control the flux and selectivity of PEMUs when they are used for membrane separations of solution species. See Krasemann et al., Langmuir 16, 287 (2000); Farhat et al., J. Am. Chem. Soc. 125, 4627 (2003); and Harris et al., Chem. Mater. 12, 1941 (2000).

1. Materials

The specifics of the materials used to carry out the studies are set forth below. The poly(glutamic acid) sodium salt (molecular weight, MW, 50,000–100,000), poly(lysine) hydrobromide) (MW 150,000–300,000), and poly(styrenesulfonic acid)(MW 70,000) were obtained from Sigma-Aldrich. The probe molecules L-ascorbic acid, D-isoascorbic acid, 3-3(3,4-dihydroxyphenyl)-L-alanine (L-DOPA), 3-3(3,4-dihydroxyphenyl)-D-alanine (D-DOPA), (S)-1-iodo-2-methylbutane, 1-iodo-2-methylpropane, 1-bromo-3-methylbutane, (S)-1-bromo-2-methylbutane, and 4,4-bipyridine were also obtained from Sigma-Aldrich. Sodium chloride and hydrogen potassium phosphate were obtained from Fisher. Potassium ferricyanide was obtained from Mallinckrodt. Solution and mean ion activities were calculated from their corresponding concentrations and appropriate activity coefficients. See Zaytsev et al., Eds., *Properties of Aqueous Solutions of Electrolytes*, CRC press, 1986–1987. Dimethyl formamide (DMF) and tetrahydrofuran (THF) were distilled and dried over molecular sieves. All other solvents were obtained from Fischer and were used without modification. Nanopure water (Barnstead, E-pure, Milli-Q 18 MΩ·cm) was used to prepare all aqueous solutions.

The poly(N-(S)alkylated-4-vinyl pyridinium iodide) and poly(N-alkylated-4-vinyl pyridinium iodide) were synthesized as follows. Poly(4-vinylpyridine)(molecular weight ~300,000) was obtained from Polysciences Inc. and 1.0 g (9.4 mmol-based on polymer repeat unit) of P4VP was dried at 110° C. for 4 hours. The dried polymer was then dissolved in dry DMF (100 mL) within a 3-neck flask that was placed in a 50° C. oil bath for 72 hours under argon while being stirred under reflux. Then, 2.24 g (11.3 mmol) of the alkylating agent was added dropwise to the P4VP solution. The reaction temperature was then raised to 80° C. under reflux for 24 hours. The product was purified by dissolving it in DMF and then reprecipitating from ethyl acetate. The precipitate was then dried in vacuo at 60° C. for 24 hours. The synthesis process produced 2.44 g alkylated P4VP which was a yield of about 85%. Fourier transfer infrared spectroscopy performed according to a method known in the art, showed the product to be about 70% alkylated.

The alkylated bipyridines (viologens) were synthesized as follows. First, 1 g (6.4 mmol) of 4,4'-bipyridine was dissolved in 30 mL of dry 1:1 volume mixture of DMF and nitromethane within a 3-neck flask. Next, 2.14 g (14.2 mmol) of the alkylating reagent was added dropwise and the reaction flask was placed into an oil bath and heated under reflux at 80° C. for 6 hours. Eventually, the reaction product precipitated out of solution. The precipitated reaction product was washed with DMF and then dried in vacuo for 24 hours at 60° C. The synthesis process produced 2.70 g of alkylated bipyridines which was a yield of about 92%. The FTIR spectra were compared to that of methyl viologen from Sigma-Aldrich and the spectra were found to be very similar except for the methylene and methine peaks that did not exist in the spectrum of the methyl viologen. Proton nuclear magnetic resonance ($^1$H NMR) spectroscopy was performed on non-optically active and optically active viologen to determine their structures. For example, $^1$H NMR spectroscopy can determine the number of different types of hydrogens present in a molecule, the relative amounts of the different types of hydrogens, the electronic environment of the different types of hydrogens, and the number of hydrogen neighbors a particular hydrogen has. The $^1$H NMR spectroscopy for the non-optically active viologen was ($D_2O$, 300 MHz,TMS): d=8.38(d, 4H); 8.95(d, 4H); 0.8(d, 12H); 1.45–1.55(m, 2H); 1.76–1.84(m, 4H); 4.5(t, 4H). The $^1$H NMR spectroscopy for the optically active viologen was ($D_2O$, 300 MHz): d=8.33(d, 4H); 8.90(d, 4H); 0.85(t, 6H); 1.43–1.50(m, 4H); 1.73–1.81 (m, 2H); 1.52(d, 6H); 4.46(d, 4H).

2. Preparation of a Multilayer on an Electrode

The working electrode upon which the multilayer was deposited was a rotating platinum disk electrode (RDE) from Pine Instruments having a 8 mm diameter. The electrode was polished with 0.05 μm alumina from Buehler, sonicated and rinsed in water. The electrode was further sonicated in a mercaptoethanesulfonic acid (MES) solution to maintain a negatively charged surface prior to the multilayer deposition. Sequential adsorption of polyelectrolytes onto the RDE at 300 rpm was performed with the aid of a STRATOSEQUENCE V robot from nanoStrata Inc. The two polymer deposition solutions contained 1 mM (based on the polymer repeat unit) polyelectrolyte, 10 mM phosphate buffer solutions (pH=7.4), and 0.25 M NaCl. Between alternating exposures to the polyelectrolytes, there were three rinses in 10 mM phosphate buffer with no NaCl added. Rinse and polymer solutions were approximately 50 mL each. The deposition time for each layer was 5 minutes and each rinse lasted for 30 seconds. The last layer, which was anionic, was deposited from a solution containing 10 mM of polymer in 10 mM NaCl for 24 hr to allow adsorption with minimal surface charge overcompensation. See Farhat et al., J. Am. Chem. Soc. 125, 4627 (2003). The coated electrode was rinsed and dried. The thicknesses of the multilayers were measured with a Gaertner Scientific L116B AUTO-GAIN ellipsometer with 632.8 nm radiation at 70° incident angle using a refractive index of 1.54 for the multilayers to be about 90 nm. The thickness measurements were confirmed using atomic force microscopy with a NANOSCOPE 4 from Digital Instruments.

3. Equipment Setup and Procedure

The permeability and selectivity of these multilayers were studied using redox electrochemical methods. The electrochemical measurements were performed using a 100 mL electrochemical cell equipped with a water jacket thermostatted to 22±0.1° C., a platinum counter electrode, and a KCl-saturated calomel electrode (SCE) against which all potentials were measured. The working electrode (i.e., the rotating platinum disk electrode) was mounted in a Pine Instruments ASR2 rotator and speed controller. All solutions were deoxygenated with argon prior to performing the electrochemical measurements. The ramp of electrical potential was generated by a Princeton Applied Research 273 potentiostat interfaced to a computer. All ascorbic acid and DOPA solutions were freshly prepared for each electrochemical run at different salt concentrations because they were susceptible to air oxidation when dissolved in aqueous solutions.

4. Results and Discussion

An example of the differential transport rate, indicated directly by the current, of L- and D-ascorbic acid through a 90 nm PGA/PL multilayer, is shown in FIG. 5 and compared to the bare electrode which showed no selectivity. The bare electrode currents may be used to subtract precisely the series resistance to mass transport caused by diffusion through a layer of stagnant liquid next to the membrane (this resistance depends on the stirring rate) to yield a membrane-limited current. See Farhat et al., J. Am. Chem. Soc. 125, 4627 (2003). Flux data from a variety of probe/multilayer combinations are summarized in Table B.

TABLE B

| Membrane | Probe | % S[c] (0.1 M NaCl) | % S (0.5 M NaCl) | % S (2.0 M NaCl) |
|---|---|---|---|---|
| PN(S)4VPI-PSS[a] | ascorbic acid | 18.9 D/L | 10.2 D/L | e |
|  | viologen | 28.6 O/N[d] | 26.0 O/N | 17.2 O/N |
| PN4VPI-PSS[b] | ascorbic acid | 0.2 D/L | 0.1 D/L | e |
|  | viologen | 0.4 O/N | 0.2 O/N | 0.2 O/N |
| PLGA-PLL | ascorbic acid | 28.1 L/D | 25.0 L/D | 17.8 L/D |
|  | DOPA | 14.1 O/N | 13.3 O/N | 11.4 O/N |
| PDGA-PDL | ascorbic acid | 28.9 D/L | 25.2 D/L | 18.7 D/L |
|  | DOPA | 13.8 D/L | 13.2 D/L | 11.7 D/L |
| PDGA-PLL | ascorbic acid | 0.4 D/L | 0.2 D/L | 0.2 D/L |
|  | DOPA | 0.3 D/L | 0.4 D/L | 0.1 D/L |
| PLGA-PDL | ascorbic acid | 0.3 D/L | 0.1 D/L | 0.4 D/L |
|  | DOPA | 0.1 D/L | 0.1 D/L | 0.2 D/L |

[a]chiral quaternized P4VP.
[b]non-chiral P4VP.
[c]% flux selectivity.
[d]ratio of chiral probe over non-chiral probe.
[e]current was too high to be measured because the multilayer was very thin.

A number of significant observations may be discerned from Table B. First, chiral multilayers produce chiral separations. Second, a multilayer made from two chiral polyelectrolytes, such as PDGA and PDL, was more selective for D-ascorbic acid than was a multilayer comprising only one chiral polyelectrolyte. It was also observed from Table B that reversing the chirality of polyelectrolytes within the multilayer inverted the selectivity for L- over D-isomers (compare PLGA-PLL and PDGA-PDL). Further, it was discovered that a combination of the L form of one polyelectrolyte and the D form of its oppositely-charged partner effectively "neutralized" the chiral selectivity. Finally, for the sake of completeness, no selectivity for any of the chiral probes was observed when multilayers were made only from non-chiral polyelectrolytes.

The enantioselectivities and permeabilities of the PEMUs set forth in Table B were compared with various literature values for other types of enantioselective membranes. Permeabilities are defined/calculated according to the following:

$$J = \frac{i}{nFA} \quad P_c = \frac{Jt}{C_{Feed}}$$

where J is the flux of the membrane in mol·cm$^{-2}$·s$^{-1}$, i is the membrane current C s$^{-1}$), n=1 is the number of electrons involved, F is Faraday's constant (96,500 C mol$^{-1}$), A is the area of membrane (0.486 cm$^2$ in the present example), $P_c$ is the permeability coefficient (cm$^2$ s$^{-1}$), t is thickness of membrane, $C_{Feed}$ is concentration of feed solution of ascorbic acid (1×10$^{-6}$ mol cm$^{-3}$). The results of the comparison are set forth in Table C wherein R1 is Yoshikawa et al., J. Membrane Sci. 108, 171 (1995); R2 is Aoki et al., J. Membrane Sci. 99, 117 (1995); R3 is Lakshmi et al., Nature 388, 758 (1997); R4 is Yoshikawa et al., Macromolecules 29, 8197 (1996); R5 is Aoki et al., Macromolecules 32, 79 (1999); R6 is Shinohara et al., Polymer 36, 2403 (1995); R7 is Aoki et al., Polymer 38, 235 (1997); R8 is Lee et al., Polymer 43, 6255 (2002); and R9 is Aoki et al., Macromolecules 29, 4192 (1996).

TABLE C

| References | Sample Ratios of Enantiomeric Permeation Rates | Typical Permeability Coefficients, $P_c$ *10$^{10}$ (cm$^2$ s$^{-1}$) |
|---|---|---|
| R1 | 1.4 | 206 |
| R2 | 1.38 | 53 |
| R3 | 5 | 1.39 |
| R4 | 1.4 | 206 |
| R5 | 3.16, 1.2 | 0.028, 28 |
| R6 (pervaporation) | 2.4, 2.58 | 1103, 775 |
| R7 | 2.7 | 7.78 |
| R8 | 1.04–1.47 | 0.47–0.39 |
| R9 | 1.27, 3.35 | 98, 46 |
| chiral PEMUs | 1.12–1.28 | 278–1944 |

The typical flux values for PEMU membranes were high, due, in part, to their thin dimensions. However, even when permeabilities (which normalize out thickness) are compared, the PEMU membranes tend to exhibit greater permeability than the reported chiral membranes set forth in Table C. For example, the permeability coefficient ($P_c$) for the PEMU membranes described herein was in the range of 278 to 1944×10$^{-10}$ cm$^2$s$^{-1}$ compared to values in the range of 0.028 to 1103×10$^{-10}$ cm$^2$s$^{-1}$ for previously reported chiral membranes which demonstrated comparable enantioselectivities.

Figure 6:
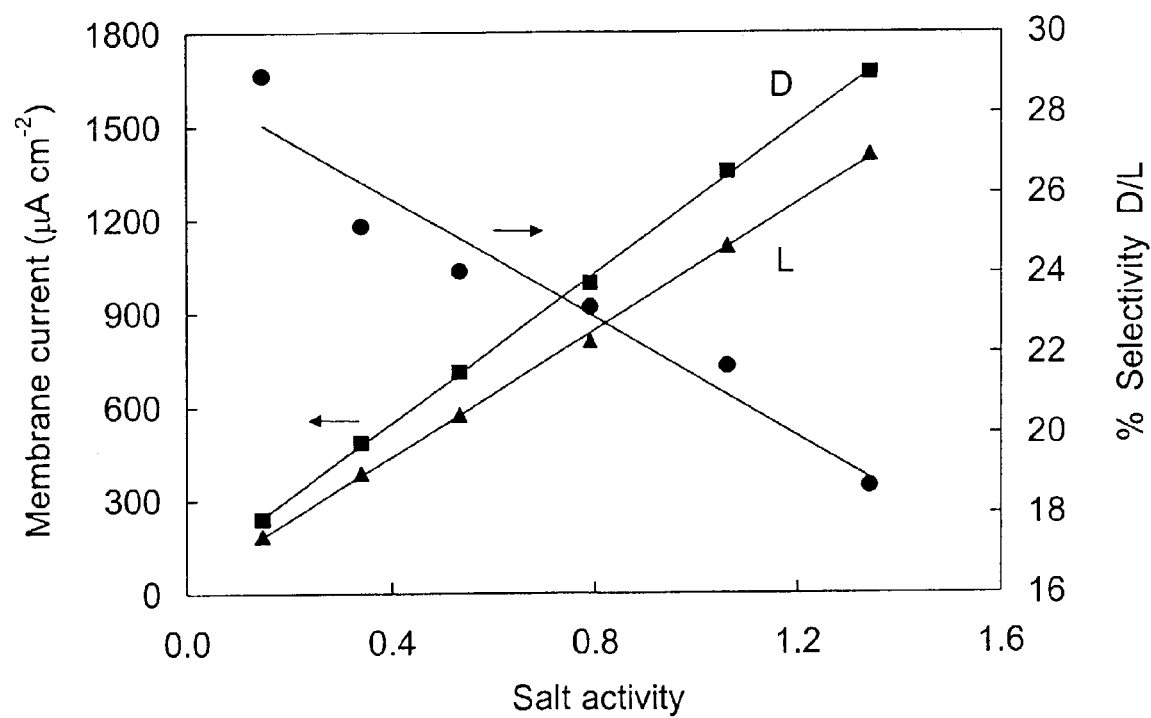
FIG. 6 is a graph depicting current density (left vertical axis) and percent selectivity for D-over L-ascorbic acid (right vertical axis) as a function of salt concentration for a PEMU comprising 16 alternating layers of PDL and PDGA exposed to a 10 mM phosphate buffer (pH 7.4) at a potential of 900 mV.

PEMU membranes offer unusual control in selectivity and flux, achieved by regulating the salt concentration. See Farhat et al., J. Am. Chem. Soc. 125, 4627 (2003). Salt swelling induces reversible "doping" of ion exchange/transport sites within PEMU membranes. For singly-charged ions, such as ascorbic acid ($pK_a$=4.17) at the pH employed in this study, the ion transport rate is linearly proportional to the salt activity, as demonstrated in FIG. 6. See Farhat et al., J. Am. Chem. Soc. 125, 4627 (2003). Higher flux comes at the expense of selectivity (also shown in FIG. 6) but the loss of selectivity is not severe. In any case, the tuning of flux with salt allows rational tradeoffs with selectivity. The selectivity trend is also represented in Table B for the other chiral probes. In the case of multiply-charged ions, such as the viologens, transport is a strongly nonlinear function of salt concentration. See Farhat et al., J. Am. Chem. Soc. 125, 4627 (2003). In order to assess the mechanism of selectivity it is instructive to consider the relationship between a steady-state flux, J, across a membrane of thickness, t, where the concentration of species is fixed on one side and zero on the other side of the membrane and solutions are "well-stirred."

$$J = \frac{\overline{D}\,\overline{C}}{t} \qquad [1]$$

where $\overline{D}$ is the diffusion coefficient of the species in the membrane and $\overline{C}$ is the membrane concentration. Percent selectivities are defined by $$\%S_{D/L} = \frac{\overline{D}_D \overline{C}_D}{\overline{D}_L \overline{C}_L} - 1 \qquad [2]$$

where the L and D subscripts refer to the respective isomer. From equation 2, flux selectivity may arise from differences in $\overline{D}$, $\overline{C}$ or both. A difference in $\overline{C}$ implies a difference in partition coefficient, a thermodynamic parameter, between isomers. A difference in $\overline{D}$ between isomers implies a difference in the rate of hopping, stemming from a possible difference in activation energies. See Farhat et al., J. Am. Chem. Soc. 125, 4627 (2003). However, a species that is strongly bound may also move more slowly (smaller $\overline{D}$, a kinetic effect).

Membrane flux is a quantitative measure of the permeation of species through a membrane. Permeation is a dynamic process. As shown in Equation 2, selectivity between two or more species permeating through a membrane is a function of both thermodynamic (concentration) and kinetic (diffusion) parameters. Therefore, it is not possible to predict, a priori, from thermodynamic data such as partitioning, the overall effectiveness of an enantioselective membrane in separating chiral compounds. For example, the chiral membrane described below exhibits only 5% thermodynamic selectivity for the two chiral forms of ascorbic acid, but the flux selectivity of the same membrane for D- and L-ascorbic acid is 25–30%.

B. Chiral Partitioning Analysis

The partitioning of L- and D-ascorbic acid into chiral multilayers (i.e., the concentrations of the chiral forms inside the multilayer) was studied using in situ Attenuated Total Reflectance Fourier Transform Infrared Spectroscopy (ATR-FTIR). See Farhat et al., J. Am. Chem. Soc. 125, 4627 (2003). The ATR-FTIR measurements of the vibrational spectra of probes entering the multilayers from solutions passing over the crystal were performed with a NICOLET NEXUS 470 fitted with a 0.5 mL capacity flow-through ATR assembly housing a 70×10×6 mm 45° zinc selenide crystal available from Specac. Multilayers were deposited on the ATR crystal while it was loaded in the flow cell by passing polyelectrolyte and rinse solutions, in an alternating manner, through the cell.

Figure 7:
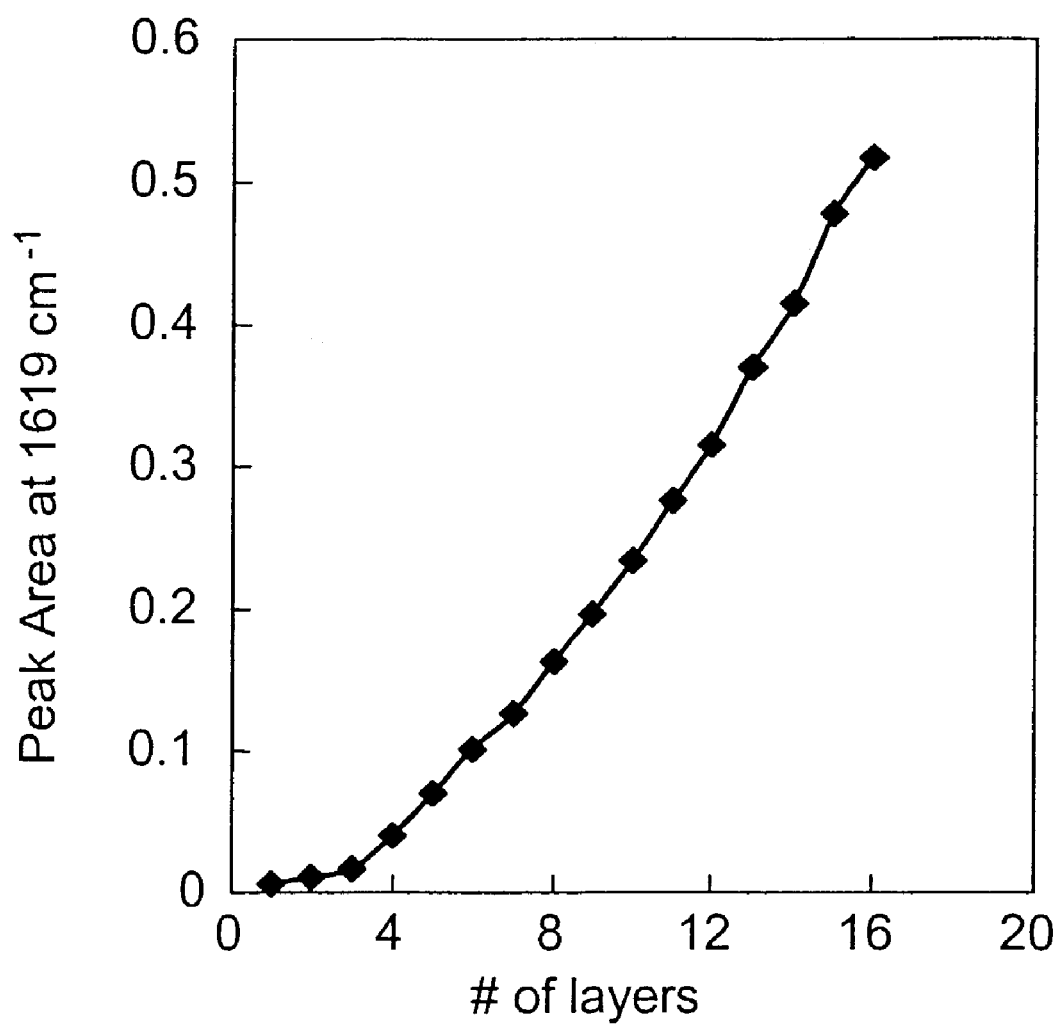
FIG. 7 is a graph depicting the in situ ATR-FTIR analysis of layer-by-layer buildup of 16 PDL-PDGA layers using 0.2 M NaCl in a 10 mM phosphate buffer (pH 7.4).

Specifically, the crystal was cleaned using 50:50 volume ratio of ethanol and $H_2O$ in a saturated salt solution. Sixteen layers of PDGA and PDL were deposited using 0.5 mM polymer in 0.2 M NaCl also containing 10 mM phosphate buffer (pH=7.4). The layer-by-layer buildup was monitored using the area of the amide peak at 1619 $cm^{-1}$ and is shown in FIG. 7. All spectra were recorded using 32 scans and 4 $cm^{-1}$ resolution. Once the multilayer was built, two different enantiomeric solutions of L- and D-ascorbic acid were passed one at a time through the ATR flow cell to monitor their concentrations in situ inside the multilayer using one of their characteristic peaks around 1650 $cm^{-1}$. The spectrum of the final multilayer with buffer solution in the flow cell was used as a background. Both solutions were 1 mM ascorbic acid in 10 mM phosphate buffer (pH=7.4) along with 0.2, 1.2 or 2 M NaCl. The 1 mM ascorbic acid solution did not show any signal when passed through the uncoated flow cell. The ratio of the concentrations of both enantiomeric forms of ascorbic acid was found to be close to 1 inside the multilayer. Specifically, the $\overline{C}_L/\overline{C}_D(\pm 2\%)$ ratio for the 0.2, 1.2, and 2 M NaCl salt concentrations were 1.038, 1.043, and 1.034, respectively. Stated another way, the equilibrium concentrations of L- and D-isomers inside a PDGA-PDL multilayer showed about a 4% difference (L over D).

Because the difference in chiral partitioning was minimally discernable using ATR-FTIR, an open tubular electrochromatographic separation (OT-CEC) of isomers was employed using PGA/PL coated capillaries with a PACE MDQ CE electrophoresis unit from Beckman Coulter of Palo Alto, Calif. See Kapnissi et al., Anal. Chem. 74, 2328 (2002); and Graul et al., Anal. Chem. 71, 4007 (1999).

Specifically, the fused silica capillary having a 50 µm i.d., a 360 µm o.d., and a polyimide outer coating was purchased from Polymicro Technologies of Phoenix, Ariz. The multilayer coatings were deposited using the rinse function (20 psi) on the Beckman CE system. Polymer deposition solutions were 0.5 mM (based on polymer repeat unit) and 0.5 M NaCl. The capillary was first conditioned by a 30-minute rinse of 1 M NaOH. Then, the phosphate buffer (pH=7.4, 20 mM) was flowed through the capillary for 10 minutes. The first monolayer was deposited using poly(ethyleneimine), a highly branched cationic polyelectrolyte, by rinsing the polymer solution through the capillary for 10 minutes followed by a buffer rinse for 5 minutes. PLGA-PLL polymer coatings were deposited with 5 minute polyelectrolyte solution rinses followed by 5 minute buffer rinses.

Figure 8:
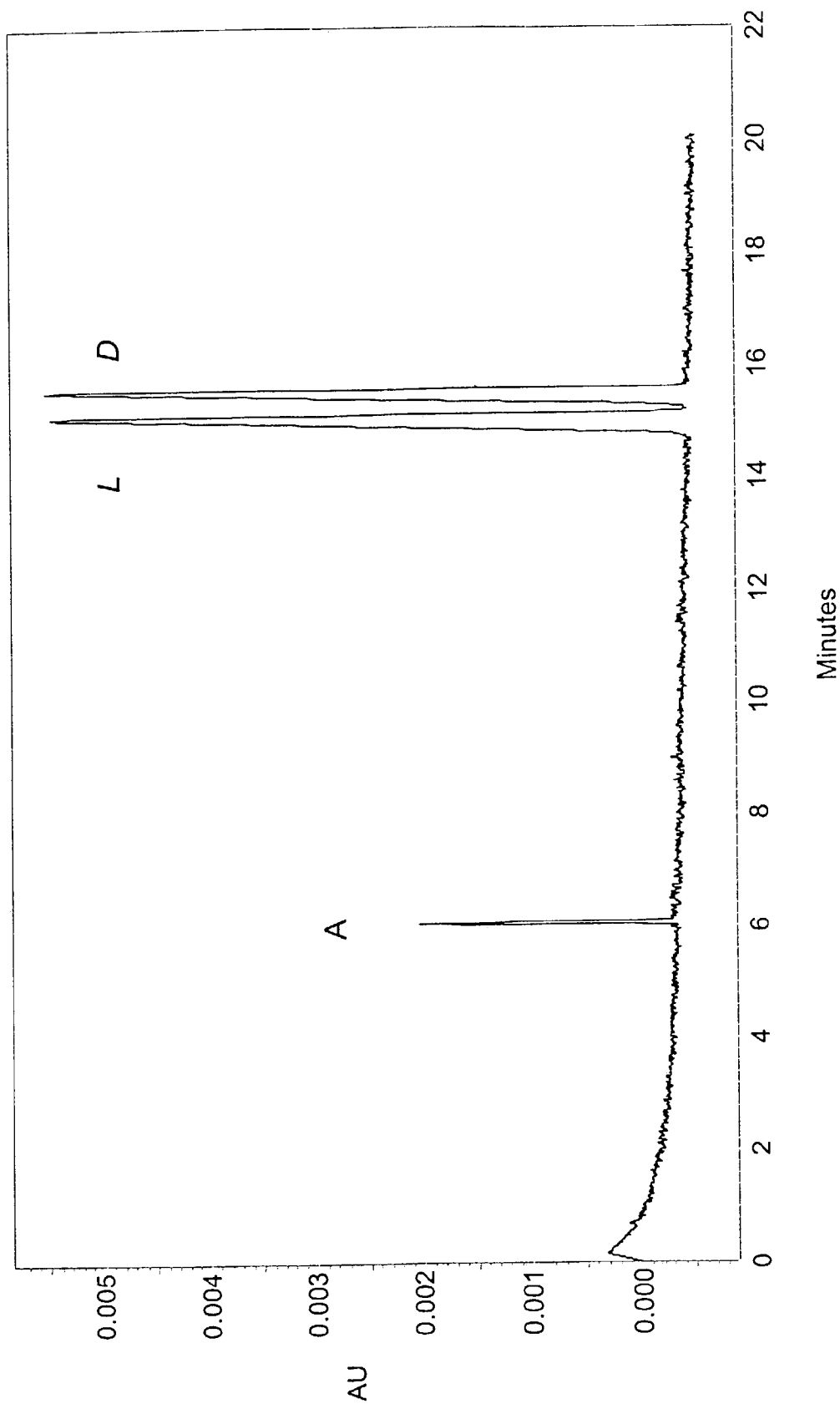
FIG. 8 is an electropherogram depicting the separation of L and D ascorbic acid using a 16 layer PLGA-PLL coating the inside of a capillary (acetone (A) was used as the neutral electroosmotic flow marker).

The electrophoresis process specifics were as follows: the capillary length was 57 cm; the length to detector was 50 cm; the applied voltage was 20 kV; UV detection was done at 254 nm; injection was done by pressure (0.5 psi, 5 sec); ascorbic acid concentration was 0.1 mM; acetone (0.1 M in phosphate buffer) was used as the neutral electroosmotic flow marker; and the tests were performed at about 25° C. FIG. 8 shows a sample electropherogram using the above conditions. The electropherograms were reproducible for at least 6 weeks and 200 runs. The number of theoretical plates for L- and D-ascorbic acid were 46,000 and 29,000 respectively. Capacity factors for L- and D-ascorbic acid were found to be 1.49 and 1.56, respectively, which yielded a selectivity factor of 1.05.

In conclusion, the results of the foregoing studies emphasize that membrane selectivity is base on flux, a dynamic parameter, and does not represent substantial differences in partitioning. In other words, it is possible to obtain much greater selectivity when performing chiral separations through chiral PEMU membranes than expected simply on the basis of partitioning.

In view of the above, it will be seen that the several objects of the invention are achieved and other advantageous results attained. It is to be understood that the above description is intended to be illustrative and not restrictive. Many embodiments will be apparent to those of skill in the art upon reading the above description. The scope of the invention should therefore be determined not with reference to the above description alone, but should be determined with reference to the claims and the full scope of equivalents to which such claims are entitled.

What is claimed is:

1. A supported membrane, the supported membrane comprising a porous substratum having a surface and a polyelectrolyte complex film on the surface of the porous substratum, the polyelectrolyte complex film having a thickness between about 10 nm and about 10,000 nm and comprising a positively-charged polyelectrolyte and a negatively-charged polyelectrolyte, and at least one of the polyelectrolytes comprises an enantiomeric excess of chiral repeat units.

2. The supported membrane of claim 1 wherein the pores have an average pore size between about 100 nm and about 10 μm.

3. A chromatographic medium comprising:
a chromatociraphic stationary phase substratum having a surface, the chromatographic stationary phase selected from the group consisting of a porous particulate chromatographic packing material, a capillary tube, and a porous continuous solid;
and a polyelectrolyte complex film on the surface of the chromatographic stationary phase substratum, the polyelectrolyte complex film having a thickness between about 10 nm and about 10,000 nm and comprising a positively-charged polyelectrolyte and a negatively-charged polyelectrolyte, wherein at least one of the positively-charged polyelectrolyte and the negatively-charged polyelectrolyte comprises an enantiomeric excess of chiral repeat units.

4. A method of chromatographically separating test enantiomers, the method comprising contacting a solution comprising test enantiomers with a chromatographic medium comprising a stationary phase substratum having a surface and an optically active polyelectrolyte complex film on the surface of the stationary phase is phase×3 substratum, wherein
the stationary phase substratum is selected from the group consisting of a porous particulate chromatographic packing material, a capillary tube, and a porous continuous solid;
the optically active polyelectrolyte complex film has a thickness between about 10 nm and about 10,000 nm and comprises a positively-charged polyelectrolyte and a negatively-charged polyelectrolyte, wherein at least one of the positively-charged polyelectrolyte and the negatively charged polyelectrolyte comprises an enantiomeric excess of chiral repeat units; and
the test enantiomers interact with the polyelectrolyte complex film on the surface of the stationary phase in an enantioselective manner.

5. The method of claim 4 wherein the stationary phase substratum is the porous particulate chromatographic packing material.

6. The method of claim 4 wherein the positively-charged polyelectrolyte and the negatively-charged polyelectrolyte comprise an enantiomeric excess of chiral repeat units.

7. The method of claim 4 wherein the positively-charged polyelectrolyte and the negatively-charged polyelectrolyte comprise an enantiomeric excess of L-chiral repeat units or the positively-charged polyelectrolyte and the negatively-charged polyelectrolyte comprise an enantiomeric excess of D-chiral repeat units.

8. The method of claim 4 wherein the positively-charged polyelectrolyte and the negatively-charge polyelectrolyte are selected from the group consisting of linear polyelectrolytes, branched polyelectrolytes, dendritic polyelectrolytes, graft polyelectrolytes, comb polyelectrolytes, and copolymers thereof.

9. The method of claim 4 wherein the polyelectrolyte comprising an enantiomeric excess of chiral repeat units is formed from chiral monomer units.

10. The method of claim 9 wherein the polyelectrolyte comprising an enantiomeric excess of chiral repeat units is poly(lysine) or poly(glutamic acid).

11. The method of claim 4 wherein the polyelectrolyte comprising an enantiomeric excess of chiral repeat units is the reaction product of a non-chiral polymer and a chiral reagent or a non-chiral reagent which introduces chirality.

12. The method of claim 11 wherein the positively-charged polyelectrolyte is the polyelectrolyte comprising an enantiomeric excess of chiral repeat units and the non-chiral polymer comprises a quaternary ammonium group, an amine group, a pyridine group, or a benzyl halogen group.

13. The method of claim 12 wherein the chiral reagent or the non-chiral reagent which introduces chirality is selected from the group consisting of a chiral alkyl halide and a chiral aryl halogen.

14. The method of claim 11 wherein the negatively-charged polyelectrolyte is the polyelectrolyte comprising an enantiomeric excess of chiral repeat units, and the negatively-charged polyelectrolyte comprises a sulfonate group or a carboxylate group.

15. The method of claim 4 wherein at least one of the negatively-charged polyelectrolyte and the positively-charged polyelectrolyte comprises a chiral cyclodextrin moiety.

* * * * *

UNITED STATES PATENT AND TRADEMARK OFFICE
CERTIFICATE OF CORRECTION

| | | |
|---|---|---|
| PATENT NO. | : 7,101,947 B2 | Page 1 of 1 |
| APPLICATION NO. | : 10/462164 | |
| DATED | : September 5, 2006 | |
| INVENTOR(S) | : Joseph B. Schlenoff et al. | |

It is certified that error appears in the above-identified patent and that said Letters Patent is hereby corrected as shown below:

Column 21, claim 3, line 35: "chromatociraphic" should read -- chromatographic --.

Column 21, claim 4, line 54: "phase is phasex3 substratum" should read -- phase substratum --.

Signed and Sealed this

Third Day of April, 2007

JON W. DUDAS
*Director of the United States Patent and Trademark Office*